United States Patent
Mederski et al.

(10) Patent No.: US 7,683,093 B2
(45) Date of Patent: Mar. 23, 2010

US007683093B2

(54) PROLINYL DERIVATIVES FOR THE TREATMENT OF THROMBOSIS

(75) Inventors: Werner Mederski, Zwingenberg (DE); Christos Tsaklakidis, Weinheim (DE); Dieter Dorsch, Ober-Ramstadt (DE); Bertram Cezanne, Moerfelden-Walldorf (DE); Johannes Gleitz, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 597 days.

(21) Appl. No.: 10/594,024

(22) PCT Filed: Mar. 4, 2005

(86) PCT No.: PCT/EP2005/002306

§ 371 (c)(1),
(2), (4) Date: Sep. 25, 2006

(87) PCT Pub. No.: WO2005/092849

PCT Pub. Date: Oct. 6, 2005

(65) Prior Publication Data

US 2007/0135507 A1  Jun. 14, 2007

(30) Foreign Application Priority Data

Mar. 26, 2004  (DE) .................. 10 2004 014 945

(51) Int. Cl.
*A61K 31/40* (2006.01)
*C07D 207/04* (2006.01)

(52) U.S. Cl. .............. 514/423; 548/530; 548/537; 548/538; 548/314.7; 514/408; 514/397

(58) Field of Classification Search ............... 548/530, 548/537, 538, 311.1, 314.7; 514/408, 423, 514/396, 397
See application file for complete search history.

(56) References Cited

U.S. PATENT DOCUMENTS

| 6,673,817 B1 | 1/2004 | Zhu |
| 7,030,141 B2 * | 4/2006 | Bigge et al. .................. 514/334 |
| 2003/0162787 A1 | 8/2003 | Bigge |

OTHER PUBLICATIONS

Bigge et al (2003): STN International HCAPLUS database, (Columbus, Ohio), Accession No. 2003:434528.*

* cited by examiner

*Primary Examiner*—Golam M Shameem
(74) *Attorney, Agent, or Firm*—Millen, White, Zelano, Branigan, P.C.

(57) ABSTRACT

Novel compounds of the formula (I), in which R, $R^1$, $R^2$, $R^3$ and $R^4$ have the meaning indicated in Patent Claim 1, are inhibitors of coagulation factor Xa and can be employed for the prophylaxis and/or therapy of thromboembolic diseases and for the treatment of tumours.

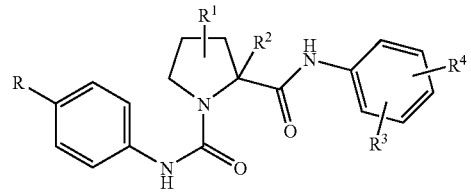

(I)

20 Claims, No Drawings

PROLINYL DERIVATIVES FOR THE TREATMENT OF THROMBOSIS

The invention relates to compounds of the formula I

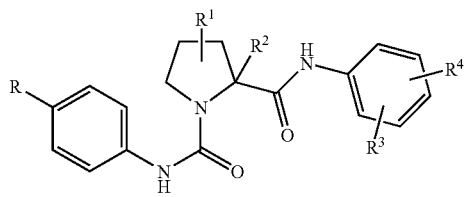

in which
R denotes Hal, —C≡C—H, —C≡C-A or OA,
$R^1$ denotes H, =O, Hal, A, OH, OA, A-COO—, Ph-$(CH_2)_n$—COO—, cycloalkyl-$(CH_2)_n$—COO—, A-CONH—, A-CONA-, Ph-CONA-, $N_3$, $NH_2$, $NO_2$, CN, COOH, COOA, $CONH_2$, CONHA, $CON(A)_2$, O-allyl, O-propargyl, O-benzyl, =N—OH, =N-OA or =$CF_2$,
$R^2$ denotes H or A,
Ph denotes phenyl which is unsubstituted or mono-, di- or trisubstituted by A, OA, OH or Hal,
$R^3$ denotes H, Hal or A,
$R^4$ denotes —$C_6H_4$—$(CH_2)_n$—$NR^5R^{5'}$, —C(=$NR^5$)$NR^4R^{5'}$,

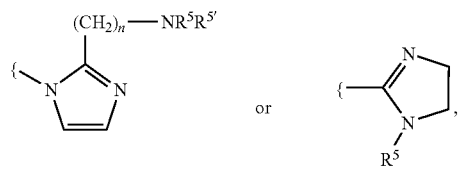

$R^5$, $R^{5'}$ each, independently of one another, denote H or A,
A denotes unbranched, branched or cyclic alkyl having 1-12 C atoms, in which, in addition, 1-7 H atoms may be replaced by F and/or chlorine,
Hal denotes F, Cl, Br or I,
n denotes 0, 1, 2 or 3,
and pharmaceutically usable derivatives, solvates, salts and stereoisomers thereof, including mixtures thereof in all ratios.

The invention had the object of finding novel compounds having valuable properties, in particular those which can be used for the preparation of medicaments.

It has been found that the compounds of the formula I and salts thereof have very valuable pharmacological properties and are well tolerated. In particular, they exhibit factor Xa-inhibiting properties and can therefore be employed for combating and preventing thromboembolic diseases, such as thrombosis, myocardial infarction, arteriosclerosis, inflammation, apoplexy, angina pectoris, restenosis after angioplasty and claudicatio intermittens.

The compounds of the formula I according to the invention may furthermore be inhibitors of the coagulation factors factor VIIa, factor IXa and thrombin in the blood coagulation cascade.

Aromatic amidine derivatives having an antithrombotic action are known, for example, from EP 0 540 051 B1, WO 98/28269, WO 00/71508, WO 00/71511, WO 00/71493, WO 00/71507, WO 00/71509, WO 00/71512, WO 00/71515 or WO 00/71516. Cyclic guanidines for the treatment of thromboembolic diseases are described, for example, in WO 97/08165.

Aromatic heterocycles having a factor Xa inhibitory activity are known, for example, from WO 96/10022. Substituted N-[(aminoiminomethyl)phenylalkyl]azaheterocyclylamides as factor Xa inhibitors are described in WO 96/40679.

Other carboxamide derivatives are known from WO 02/48099 and WO 02/57236, other pyrrolidine derivatives are described in WO 02/100830.

Further heterocyclic derivatives are known from WO 03/045912.

Pyrrolidine derivatives as inhibitors of endothelin converting enzyme are known from WO 02/06222.

Pyrrolidine derivatives as cholecystokinin and gastrin inhibitors are described in U.S. Pat. No. 5,340,801. Other pyrrolidine derivatives are known from WO 01/044192.

The antithrombotic and anticoagulant effect of the compounds according to the invention is attributed to the inhibitory action against activated coagulation protease, known by the name factor Xa, or to the inhibition of other activated serine proteases, such as factor VIIa, factor IXa or thrombin.

Factor Xa is one of the proteases involved in the complex process of blood coagulation. Factor Xa catalyses the conversion of prothrombin into thrombin. Thrombin cleaves fibrinogen into fibrin monomers, which, after crosslinking, make an elementary contribution to thrombus formation. Activation of thrombin may result in the occurrence of thromboembolic diseases. However, inhibition of thrombin may inhibit the fibrin formation involved in thrombus formation.

The inhibition of thrombin can be measured, for example by the method of G. F. Cousins et al. in *Circulation* 1996, 94, 1705-1712.

Inhibition of factor Xa can thus prevent the formation of thrombin.

The compounds of the formula I according to the invention and salts thereof engage in the blood coagulation process by inhibiting factor Xa and thus inhibit the formation of thrombuses.

The inhibition of factor Xa by the compounds according to the invention and the measurement of the anticoagulant and antithrombotic activity can be determined by conventional in-vitro or in-vivo methods. A suitable method is described, for example, by J. Hauptmann et al. in *Thrombosis and Haemostasis* 1990, 63, 220-223.

The inhibition of factor Xa can be measured, for example by the method of T. Hara et al. in *Thromb. Haemostas.* 1994, 71, 314-319.

Coagulation factor VIIa initiates the extrinsic part of the coagulation cascade after binding to tissue factor and contributes to the activation of factor X to give factor Xa. Inhibition of factor VIIa thus prevents the formation of factor Xa and thus subsequent thrombin formation.

The inhibition of factor VIIa by the compounds according to the invention and the measurement of the anticoagulant and antithrombotic activity can be determined by conventional in-vitro or in-vivo methods. A conventional method for the measurement of the inhibition of factor VIIa is described, for example, by H. F. Ronning et al. in *Thrombosis Research* 1996, 84, 73-81.

Coagulation factor IXa is generated in the intrinsic coagulation cascade and is likewise involved in the activation of factor X to give factor Xa. Inhibition of factor IXa can therefore prevent the formation of factor Xa in a different way.

The inhibition of factor IXa by the compounds according to the invention and the measurement of the anticoagulant and antithrombotic activity can be determined by conventional in-vitro or in-vivo methods. A suitable method is described, for example, by J. Chang et al. in *Journal of Biological Chemistry* 1998, 273, 12089-12094.

The compounds according to the invention may furthermore be used for the treatment of tumours, tumour diseases and/or tumour metastases. A correlation between tissue factor TF/factor VIIa and the development of various types of cancer has been indicated by T. Taniguchi and N. R. Lemoine in Biomed. Health Res. (2000), 41 (Molecular Pathogenesis of Pancreatic Cancer), 57-59.

The publications listed below describe an antitumoural action of TF-VII and factor Xa inhibitors for various types of tumour:
K. M. Donnelly et al. in Thromb. Haemost. 1998; 79: 1041-1047;
E. G. Fischer et al. in J. Clin. Invest. 104: 1213-1221 (1999);
B. M. Mueller et al. in J. Clin. Invest. 101: 1372-1378 (1998);
M. E. bromoberg et al. in Thromb. Haemost. 1999; 82: 88-92

The compounds of the formula I can be employed as medicament active ingredients in human and veterinary medicine, in particular for the treatment and prevention of thromboembolic diseases, such as thrombosis, myocardial infarction, arteriosclerosis, inflammation, apoplexy, angina pectoris, restenosis after angioplasty, claudicatio intermittens, venous thrombosis, pulmonary embolism, arterial thrombosis, myocardial ischaemia, unstable angina and strokes based on thrombosis.

The compounds according to the invention are also employed for the treatment or prophylaxis of atherosclerotic diseases, such as coronary arterial disease, cerebral arterial disease or peripheral arterial disease.

The compounds are also employed in combination with other thrombolytic agents in myocardial infarction, furthermore for prophylaxis for reocclusion after thrombolysis, percutaneous transluminal angioplasty (PTCA) and coronary bypass operations.

The compounds according to the invention are furthermore used for the prevention of rethrombosis in microsurgery, furthermore as anticoagulants in connection with artificial organs or in haemodialysis.

The compounds are furthermore used in the cleaning of catheters and medical aids in patients in vivo, or as anticoagulants for the preservation of blood, plasma and other blood products in vitro. The compounds according to the invention are furthermore used in diseases in which blood coagulation makes a crucial contribution towards the course of the disease or represents a source of secondary pathology, such as, for example, in cancer, including metastasis, inflammatory diseases, including arthritis, and diabetes.

The compounds according to the invention are furthermore used for the treatment of migraine (F. Morales-Asin et al., Headache, 40, 2000, 45-47). In addition, they can be used for the treatment of tinnitus. The use of anticoagulants in tinnitus therapy is described by R. Mora et al. in International Tinnitus Journal (2003), 9(2), 109-111.

In the treatment of the diseases described, the compounds according to the invention are also employed in combination with other thrombolytically active compounds, such as, for example, with the "tissue plasminogen activator" t-PA, modified t-PA, streptokinase or urokinase. The compounds according to the invention are administered either at the same time as or before or after the other substances mentioned.

Particular preference is given to simultaneous administration with aspirin in order to prevent recurrence of the thrombus formation.

The compounds according to the invention are also used in combination with blood platelet glycoprotein receptor (IIb/IIIa) antagonists, which inhibit blood platelet aggregation.

The invention relates to the compounds of the formula I and salts thereof and to a process for the preparation of compounds of the formula I according to claims 1-16 and pharmaceutically usable derivatives, solvates, salts and stereoisomers thereof, characterised in that a) a compound of the formula II

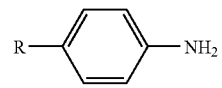

II in which R has the meaning indicated in claim 1, is reacted with a chloroformate derivative to give an intermediate carbamate derivative, which is subsequently reacted with a compound of the formula III

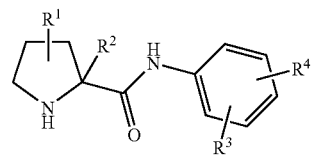

III in which
$R^1$, $R^2$, $R^3$ and $R^4$ have the meaning indicated in claim 1,
or
b) a compound of the formula III
is reacted with a compound of the formula IV

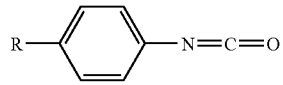

IV in which
R has the meaning indicated in claim 1,
or
c) a compound of the formula V

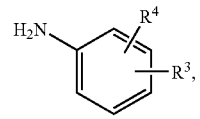

V in which $R^3$ and $R^4$ have the meaning indicated in claim 1, is reacted with a compound of the formula VI

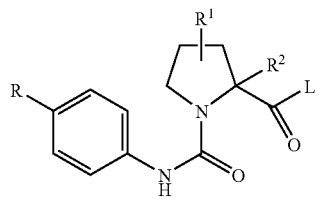

in which
L denotes Cl, Br, I or a free or reactively functionally modified OH group and
R, $R^1$ and $R^2$ have the meanings indicated in claim 1,
and/or
a base or acid of the formula I is converted into one of its salts.

The invention also relates to the optically active forms (stereoisomers), the enantiomers, the racemates, the diastereomers and the hydrates and solvates of these compounds. The term solvates of the compounds is taken to mean adductions of inert solvent molecules onto the compounds which form owing to their mutual attractive force. Solvates are, for example, mono- or dihydrates or alcoholates.

The term pharmaceutically usable derivatives is taken to mean, for example, the salts of the compounds according to the invention and so-called prodrug compounds.

The term prodrug derivatives is taken to mean compounds of the formula I which have been modified with, for example, alkyl or acyl groups, sugars or oligopeptides and which are rapidly cleaved in the organism to form the active compounds according to the invention.

These also include biodegradable polymer derivatives of the compounds according to the invention, as described, for example, in Int. J. Pharm. 115, 61-67 (1995).

The invention also relates to mixtures of the compounds of the formula I according to the invention, for example mixtures of two diastereomers, for example in the ratio 1:1, 1:2, 1:3, 1:4, 1:5, 1:10, 1:100 or 1:1000.

These are particularly preferably mixtures of stereoisomeric compounds.

For all radicals which occur more than once, such as, for example, A, their meanings are independent of one another.

Above and below, the radicals and parameters R, $R^1$, $R^2$, $R^3$, $R^4$ have the meanings indicated in the case of the formula I, unless expressly stated otherwise.

A denotes alkyl, is unbranched (linear) or branched, and has 1, 2, 3, 4, 5, 6, 7, 8, 9, 10, 11 or 12 C atoms. A preferably denotes methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, furthermore preferably, for example, trifluoromethyl. A also denotes cycloalkyl.

Cycloalkyl preferably denotes cyclopropyl, cyclobutyl, cyclopentyl, cyclohexyl or cycloheptyl.

A therefore preferably also denotes cyclopentylmethyl, cyclohexylmethyl, A very particularly preferably denotes alkyl having 1, 2, 3, 4, 5 or 6 C atoms, preferably methyl, ethyl, propyl, isopropyl, butyl, isobutyl, sec-butyl, tert-butyl, pentyl, hexyl, trifluoromethyl, pentafluoroethyl or 1,1,1-trifluoroethyl.

R preferably denotes Hal or —C≡C—H.

$R^1$ preferably denotes H, =O (carbonyl oxygen), Hal, A, OH or OA, particularly preferably OH or OA.
$R^2$ preferably denotes H.
$R^3$ preferably denotes H or Hal.
$R^4$ preferably denotes

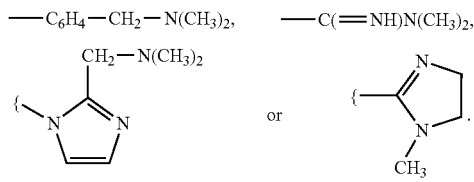

$R^5$, $R^{5'}$ preferably each, independently of one another, denote H or alkyl having 1, 2, 3, 4, 5 or 6 C atoms.

The compounds of the formula I can have one or more chiral centres and may therefore occur in various stereoisomeric forms. The formula I encompasses all these forms.

Accordingly, the invention relates, in particular, to the compounds of the formula I in which at least one of the said radicals has one of the preferred meanings indicated above. Some preferred groups of compounds can be expressed by the following sub-formulae Ia to Ig, which conform to the formula I and in which the radicals not designated in greater detail have the meaning indicated in the case of the formula I, but in which
in Ia R denotes Hal or —C≡C—H;
in Ib $R^1$ denotes H, =O, Hal, A, OH or OA;
in Ic $R^1$ denotes OH or OA;
in Id $R^3$ denotes H or Hal;
in Ie $R^5$, $R^{5'}$ each, independently of one another, denote H or alkyl having 1, 2, 3, 4, 5 or 6 C atoms;
in If $R^3$ denotes H or alkyl having 1, 2, 3, 4, 5 or 6 C atoms;
in Ig R denotes Hal or —C≡C—H,
$R^1$ denotes OH or OA
$R^2$ denotes H or A,
$R^3$ denotes H or Hal,
$R^4$ denotes —$C_6H_4$—$(CH_2)_n$—$NR^5R^{5'}$, —$C(=NR^5)NR^4R^{5'}$,

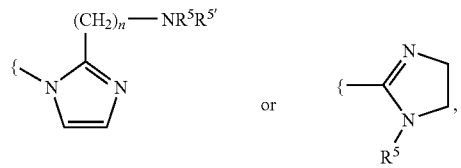

$R^5$, $R^{5'}$ each, independently of one another, denote H or A,
A denotes unbranched, branched or cyclic alkyl having 1-12 C atoms, in which, in addition, 1-7 H atoms may be replaced by F and/or chlorine,
Hal denotes F, Cl, Br or I,
n denotes 0, 1, 2 or 3;

and pharmaceutically usable derivatives, solvates and stereoisomers thereof, including mixtures thereof in all ratios.

The compounds of the formula I and also the starting materials for the preparation thereof are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants which are known per se, but are not mentioned here in greater detail.

If desired, the starting materials can also be formed in situ, so that they are not isolated from the reaction mixture, but instead are immediately converted further into the compounds of the formula I.

Compounds of the formula I can preferably be obtained by reacting compounds of the formula II with a chloroformate derivative, for example 4-nitrophenyl chloroformate, to give an intermediate carbamate and subsequently with compounds of the formula III.

The reaction is generally carried out in an inert solvent, in the presence of an acid-binding agent, preferably an alkali or alkaline earth metal hydroxide, carbonate or bicarbonate or another salt of a weak acid of the alkali or alkaline earth metals, preferably of potassium, sodium, calcium or caesium. The addition of an organic base, such as triethylamine, dimethylaniline, pyridine or quinoline, may also be favourable. Depending on the conditions used, the reaction time is between a few minutes and 14 days, the reaction temperature is between about 0° and 150°, normally between 20° and 130°.

Examples of suitable inert solvents are water; hydrocarbons, such as hexane, petroleum ether, benzene, toluene or xylene; chlorinated hydrocarbons, such as trichloroethylene, 1,2-dichloroethane, tetrachloromethane, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

The starting compounds of the formulae II and III are generally known. If they are novel, however, they can be prepared by methods known per se.

Compounds of the formula I can also be obtained by reacting compounds of the formula III with compounds of the formula IV.

This is carried out under conditions as described above.

The starting compounds of the formula IV are generally known. If they are novel, however, they can be prepared by methods known per se.

Compounds of the formula I can also be obtained by reacting compounds of the formula V with compounds of the formula VI.

In the compounds of the formula VI, L preferably denotes Cl, Br, I or a reactively modified OH group, such as, for example, an activated ester, an imidazolide or alkylsulfonyloxy having 1-6 C atoms (preferably methylsulfonyloxy or trifluoromethylsulfonyloxy) or arylsulfonyloxy having 6-10 C atoms (preferably phenyl- or p-tolylsulfonyloxy).

Radicals of this type for activation of the carboxyl group in typical acylation reactions are described in the literature (for example in the standard works, such as Houben-Weyl, Methodn der organischen Chemie [Methods of Organic Chemistry], Georg-Thieme-Verlag, Stuttgart;).

Activated esters are advantageously formed in situ, for example by addition of HOBt or N-hydroxysuccinimide.

The reaction is generally carried out in an inert solvent, in the presence of an acid-binding agent, preferably an alkali or alkaline earth metal hydroxide, carbonate or bicarbonate or another salt of a weak acid of the alkali or alkaline earth metals, preferably of potassium, sodium, calcium or caesium. The addition of an organic base, such as triethylamine, dimethylaniline, pyridine or quinoline, or an excess of the amine component of the formula IV may also be favourable. Depending on the conditions used, the reaction time is between a few minutes and 14 days, the reaction temperature is between about 0° and 150°, normally between 20° and 130°. Examples of suitable inert solvents are hydrocarbons, such as hexane, petroleum ether, benzene, toluene or xylene; chlorinated hydrocarbons, such as trichloroethylene, 1,2-dichloroethane, tetrachloromethane, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Esters can be saponified, for example, using acetic acid or using NaOH or KOH in water, water/THF or water/dioxane at temperatures between 0 and 100°.

Pharmaceutical Salts and Other Forms

The said compounds according to the invention can be used in their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds of the formula I are for the most part prepared by conventional methods. If the compound of the formula I contains a carboxyl group, one of its suitable salts can be formed by reacting the compound with a suitable base to give the corresponding base-addition salt. Such bases are, for example, alkali metal hydroxides, including potassium hydroxide, sodium hydroxide and lithium hydroxide; alkaline earth metal hydroxides, such as barium hydroxide and calcium hydroxide; alkali metal alkoxides, for example potassium ethoxide and sodium propoxide; and various organic bases, such as piperidine, diethanolamine and N-methylglutamine. The aluminium salts of the compounds of the formula I are likewise included. In the case of certain compounds of the formula I, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoarylsulfonates, such as ethanesulfonate, toluenesulfonate and benzenesulfonate, and other organic acids and corresponding salts thereof, such as acetate, trifluoroacetate, tartrate, maleate, succinate, citrate, benzoate, salicylate, ascorbate and the like. Accordingly, pharmaceutically acceptable acid-addition salts of the compounds of the formula I include the following: acetate, adipate, alginate, arginate, aspartate, benzoate, benzenesulfonate (besylate), bisulfate, bisulfite, bromide, butyrate, camphorate, camphorsulfonate, caprylate, chloride, chlorobenzoate, citrate, cyclopentanepropionate, digluconate, dihydrogenphosphate, dinitrobenzoate, dodecylsulfate, ethanesulfonate, fumarate, galacterate (from mucic acid), galacturoriate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, isobutyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction.

Furthermore, the base salts of the compounds according to the invention include aluminium, ammonium, calcium, copper, iron(III), iron(II), lithium, magnesium, manganese(III), manganese(II), potassium, sodium and zinc salts, but this is not intended to represent a restriction. Of the above-mentioned salts, preference is given to ammonium; the alkali metal salts sodium and potassium, and the alkaline earth metal salts calcium and magnesium. Salts of the compounds of the formula I which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzylethylenediamine (benzathine), dicyclohexylamine, diethanolamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris(hydroxymethyl)methylamine (tromethamine), but this is not intended to represent a restriction.

Compounds of the present invention which contain basic nitrogen-containing groups can be quaternised using agents such as $(C_1-C_4)$alkyl halides, for example methyl, ethyl, isopropyl and tert-butyl chloride, bromide and iodide; di$(C_1-C_4)$ alkyl sulfates, for example dimethyl, diethyl and diamyl sulfate; $(C_{10}-C_{18})$alkyl halides, for example decyl, dodecyl, lauryl, myristyl and stearyl chloride, bromide and iodide; and aryl$(C_1-C_4)$alkyl halides, for example benzyl chloride and phenethyl bromide. Both water- and oil-soluble compounds according to the invention can be prepared using such salts.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate and tromethamine, but this is not intended to represent a restriction.

The acid-addition salts of basic compounds of the formula I are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts otherwise correspond to the respective free base forms thereof.

As mentioned, the pharmaceutically acceptable base-addition salts of the compounds of the formula I are formed with metals or amines, such as alkali metals and alkaline earth metals or organic amines. Preferred metals are sodium, potassium, magnesium and calcium. Preferred organic amines are N,N'-dibenzylethylenediamine, chloroprocaine, choline, diethanolamine, ethylenediamine, N-methyl-D-glucamine and procaine.

The base-addition salts of acidic compounds according to the invention are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts otherwise correspond to the respective free acid forms thereof.

If a compound according to the invention contains more than one group which is capable of forming pharmaceutically acceptable salts of this type, the invention also encompasses multiple salts. Typical multiple salt forms include, for example, bitartrate, diacetate, difumarate, dimeglumine, diphosphate, disodium and trihydrochloride, but this is not intended to represent a restriction.

With regard to that stated above, it can be seen that the expression "pharmaceutically acceptable salt" in the present connection is taken to mean an active ingredient which comprises a compound of the formula I in the form of one of its salts, in particular if this salt form provides the active ingredient with improved pharmacokinetic properties compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

Compounds of the formula I according to the invention may be chiral owing to their molecular structure and may accordingly occur in various enantiomeric forms. They can therefore exist in racemic or in optically active form.

Since the pharmaceutical activity of the racemates or stereoisomers of the compounds according to the invention may differ, it may be desirable to use the enantiomers. In these cases, the end product or even the intermediates can be separated into enantiomeric compounds by chemical or physical measures known to the person skilled in the art or even employed as such in the synthesis.

In the case of racemic amines, diastereomers are formed from the mixture by reaction with an optically active resolving agent. Examples of suitable resolving agents are optically active acids, such as the R and S forms of tartaric acid, diacetyltartaric acid, dibenzoyltartaric acid, mandelic acid, malic acid, lactic acid, suitably N-protected amino acids (for example N-benzoylproline or N-benzenesulfonylproline), or the various optically active camphorsulfonic acids. Also advantageous is chromatographic enantiomer resolution with the aid of an optically active resolving agent (for example dinitrobenzoylphenylglycine, cellulose triacetate or other derivatives of carbohydrates or chirally derivatised methacrylate polymers immobilised on silica gel). Suitable eluents for this purpose are aqueous or alcoholic solvent mixtures, such as, for example, hexane/isopropanol/acetonitrile, for example in the ratio 82:15:3.

The invention furthermore relates to the use of the compounds of the formula I and/or physiologically acceptable salts thereof for the preparation of a medicament (pharmaceutical composition), in particular by non-chemical methods. They can be converted here into a suitable dosage form together with at least one solid, liquid and/or semi-liquid excipient or adjuvant and, if desired, in combination with one or more further active ingredients.

The invention furthermore relates to medicaments comprising at least one compound of the formula I and/or pharmaceutically usable derivatives, solvates and stereoisomers thereof, including mixtures thereof in all ratios, and optionally excipients and/or adjuvants.

Pharmaceutical formulations can be administered in the form of dosage units which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes which are known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbant, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tableting machine, giving lumps of non-uniform shape which are broken up to form granules. The granules can be lubricated by addition of stearic acid, a stearate salt, talc or mineral oil in order to prevent sticking to the tablet casting moulds. The lubricated mixture is then pressed to give tablets. The compounds according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a prespecified amount of the compound. Syrups can be prepared by dissolving the compound in an aqueous solution with a suitable flavour, while elixirs are prepared using a non-toxic alcoholic vehicle. Suspensions can be formulated by dispersion of the compound in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds of the formula I and salts, solvates and physiologically functional derivatives thereof can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds of the formula I and the salts, solvates and physiologically functional derivatives thereof can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The compounds may furthermore be coupled to a class of biodoegradable polymers which are suitable for achieving controlled release of a medicament, for example polylactic acid, poly-epsilon-caprolactone, polyhydroxybutyric acid, polyorthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base.

Pharmaceutical formulations adapted for topical application to the eye include eye drops, in which the active ingredient is dissolved or suspended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose.

Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multidose containers, for example sealed ampoules and vials, and stored in the freeze-dried (lyophilised) state, so that only the addition of the sterile carrier liquid, for example water for injection purposes, immediately before use is necessary.

Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound of the formula I depends on a number of factors, including, for example, the age and weight of the animal, the precise condition which requires treatment, and its severity, the nature of the formulation and the method of administration, and is ultimately determined by the treating doctor or vet. However, an effective amount of a compound according to the invention is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as a single dose per day or more usually in a series of part-doses (such as, for example, two, three, four, five or six) per day, so that the total daily dose is the same. An effective amount of a salt or solvate or of a physiologically functional derivative thereof can be determined as the fraction of the effective amount of the compound according to the invention per se.

The compounds of the formula I and physiologically acceptable salts thereof can be used for combating and preventing thromboembolic diseases, such as thrombosis, myocardial infarction, arteriosclerosis, inflammation, apoplexy, angina pectoris, restenosis after angioplasty, claudicatio intermittens, migraine, tinnitus, tumours, tumour diseases and/or tumour metastases.

The invention furthermore relates to medicaments comprising at least one compound of the formula I and/or pharmaceutically usable derivatives, solvates, salts and stereoisomers thereof, including mixtures thereof in all ratios, and at least one further medicament active ingredient.

The invention also relates to a set (kit) consisting of separate packs of (a) an effective amount of a compound of the formula I and/or pharmaceutically usable derivatives, solvates, salts and stereoisomers thereof, including mixtures thereof in all ratios, and (b) an effective amount of a further medicament active ingredient.

The set comprises suitable containers, such as boxes, individual bottles, bags or ampoules. The set may, for example, comprise separate ampoules, each containing an effective amount of a compound of the formula I and/or pharmaceutically usable derivatives, solvates, salts and stereoisomers thereof, including mixtures thereof in all ratios, and an effective amount of a further medicament active ingredient in dissolved or lyophilised form.

The invention furthermore relates to the use of compounds of the formula I and/or pharmaceutically usable derivatives, solvates, salts and stereoisomers thereof, including mixtures thereof in all ratios, for the preparation of a medicament for the treatment of thromboses, myocardial infarction, arteriosclerosis, inflammation, apoplexy, angina pectoris, restenosis after angioplasty, claudicatio intermittens, migraine, tinnitus, tumours, tumour diseases and/or tumour metastases, in combination with at least one further medicament active ingredient.

Above and below, all temperatures are indicated in ° C. In the following examples, "conventional work-up" means: water is added if necessary, the pH is adjusted, if necessary, to values between 2 and 10, depending on the constitution of the end product, the mixture is extracted with ethyl acetate or dichloromethane, the phases are separated, the organic phase is dried over sodium sulfate and evaporated, and the product is purified by chromatography on silica gel and/or by crystallisation. Rf values on silica gel; eluent: ethyl acetate/methanol 9:1.

Mass spectrometry (MS): EI (electron impact ionisation) M+

ESI (electrospray ionisation) (M+H)+ (unless indicated otherwise)

EXAMPLE 1

N-1-[(4-Chlorophenyl)]-N-2-{[4-(2-{dimethylaminomethyl}phenyl)-phenyl]}-(2R,4R)-4-hydroxypyrrolidine-1,2-dicarboxamide ("A1")

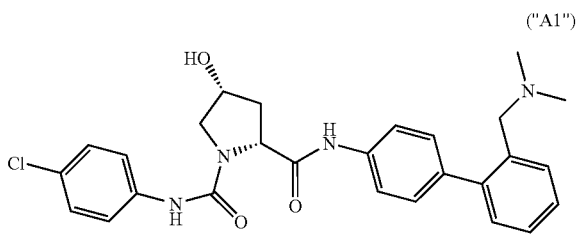

The preparation is carried out analogously to the following scheme

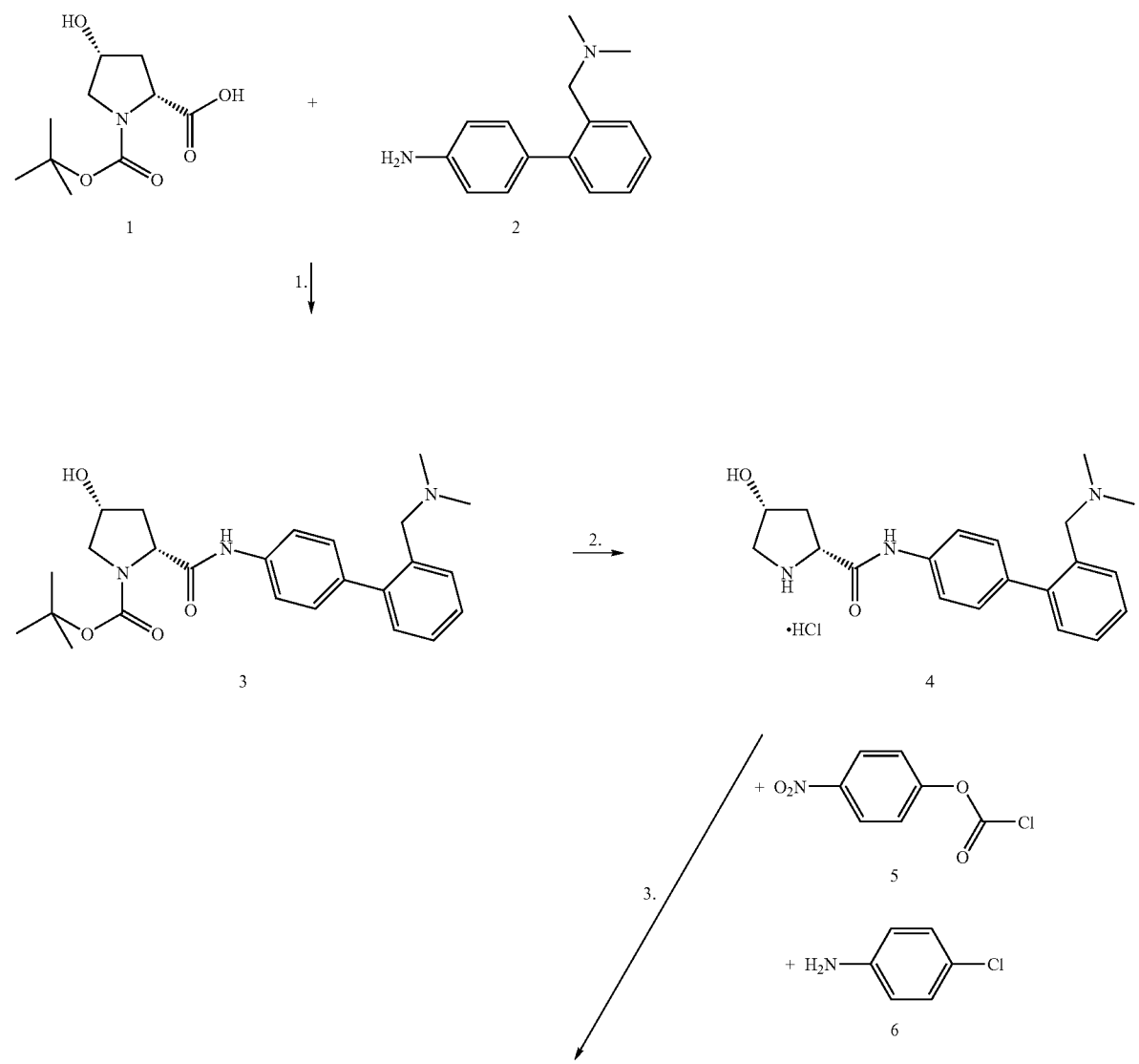

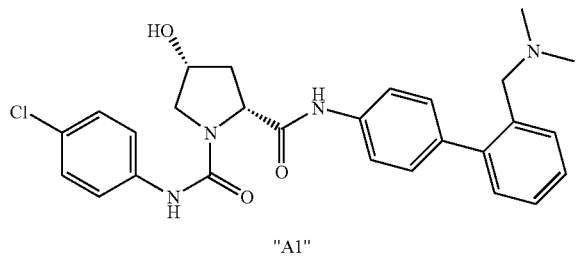

"A1"

1. 4 mmol of 2'-dimethylaminomethylbiphenyl-4-ylamine 2 and 4 mmol of ethyl 2-ethoxy-1,2-dihydroquinoline-1-carboxylate are added successively with stirring at room temperature to 4 mmol of BOC-4-hydroxyproline 1 as suspension in 15 ml of toluene. The mixture is subsequently stirred at this temperature for 18 h. The mixture is then subjected to conventional work-up, giving BOC-proline biphenylamine derivative 3 as crude product.
2. 3 mmol of 3 are dissolved in 20 ml of dioxane, and 20 ml of 4 N HCl in dioxane are added at room temperature, and the mixture is stirred at this temperature for 2 h. The mixture is then subjected to conventional work-up, giving the proline biphenylamine hydrochloride derivative 4 as crude product.
3. 1 mmol of 4-nitrophenyl chloroformate 5, 1 mmol of 4-chloroaniline and 1 mmol of pyridine in 10 ml of dichloromethane are stirred at room temperature for 1 h under a nitrogen atmosphere. 1 mmol of 4 and 3 mmol of N-ethyl-diisopropylamine in 5 ml of dichloromethane are subsequently added. The resultant suspension is stirred at room temperature for a further 2 h. The mixture is then subjected to conventional work-up, giving "A1".

The following compounds are obtained analogously
N-1-[(4-ethynylphenyl)]-N-2-{[4-(2-{dimethylaminomethyl}phenyl)phenyl]}-(2R,4R)-4-hydroxypyrrolidine-1,2-dicarboxamide,
N-1-[(4-chlorophenyl)]-N-2-{[2-fluoro-4-(2-{dimethylaminomethyl}-phenyl)phenyl]}-(2R,4R)-4-hydroxypyrrolidine-1,2-dicarboxamide,
N-1-[(4-ethynylphenyl)]-N-2-{[2-fluoro-4-(2-{dimethylaminomethyl}-phenyl)phenyl]}-(2R,4R)-4-hydroxypyrrolidine-1,2-dicarboxamide,
N-1-[(4-chlorophenyl)]-N-2-[(4-(2-dimethylaminomethylimidazol-1-yl)phenyl)]-(2R,4R)-4-hydroxypyrrolidine-1,2-dicarboxamide

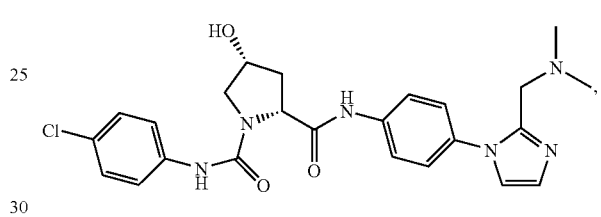

N-1-[(4-ethynylphenyl)]-N-2-[(4-(2-dimethylaminomethylimidazol-1-yl)phenyl)]-(2R,4R)-4-hydroxypyrrolidine-1,2-dicarboxamide,
N-1-[(4-chlorophenyl)]-N-2-[(2-fluoro-4-(2-dimethylaminomethylimidazol-1-yl)phenyl)]-(2R,4R)-4-hydroxypyrrolidine-1,2-dicarboxamide,
N-1-[(4-ethynylphenyl)]-N-2-[(2-fluoro-4-(2-dimethylaminomethylimidazol-1-yl)phenyl)]-(2R,4R)-4-hydroxypyrrolidine-1,2-dicarboxamide.

EXAMPLE 2

The preparation of the intermediate N-1-[(4-chlorophenyl)]-N-2-[(4-cyanophenyl)]-(2R,4R)-4-hydroxypyrrolidine-1,2-dicarboxamide ("7") is carried out analogously to Example 1 and as shown in the following scheme.

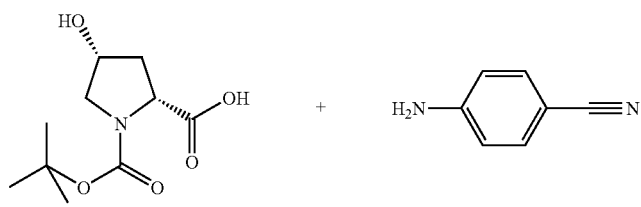

-continued

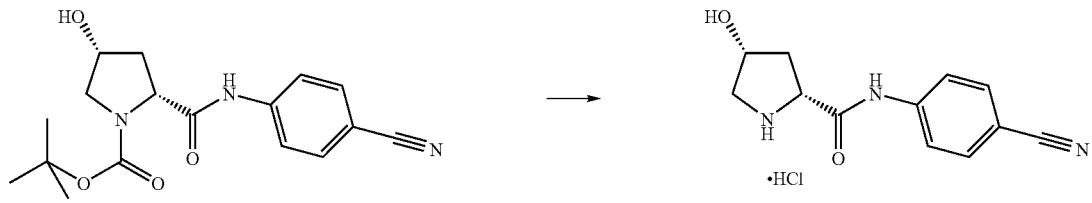

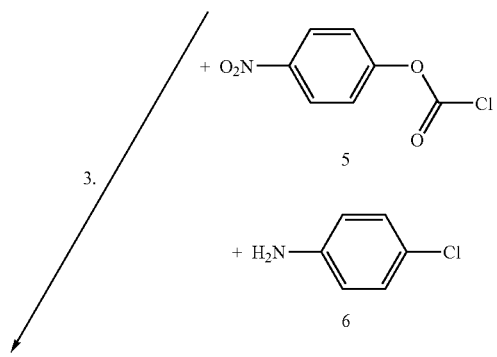

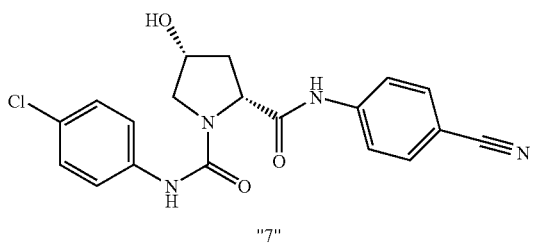

"7"

EXAMPLE 3

Preparation of the intermediate N-1-[(4-chlorophenyl)]-N-2-[(4-methoxycarbonimidoylphenyl)]-(2R,4R)-4-hydroxypyrrolidine-1,2-dicarboxamide ("8")

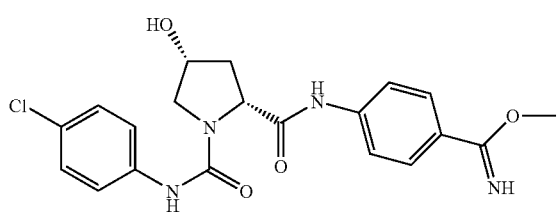

"8"

Compound "7" is dissolved in dry methanol. At 0°, the solution is saturated with HCl gas. The mixture is stirred at room temperature for a further 12 h, and conventional work-up gives "8".

EXAMPLE 4

N-1-[(4-Chlorophenyl)]-N-2-[(4-(N,N-dimethylamidino)phenyl)]-(2R,4R)-4-hydroxypyrrolidine-1,2-dicarboxamide ("A4")

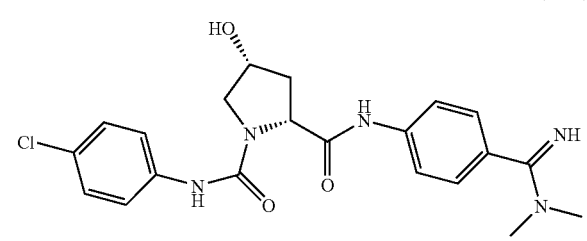

("A4")

Compound "8" is dissolved in dry methanol. 5 equivalents of dimethylamine (2M in methanol) are added, and the mixture is heated under reflux. After 1 hour, the mixture is subjected to conventional work-up, giving "A4".

The following compounds are obtained analogously

N-1-[(4-ethynylphenyl)]-N-2-[(4-(N,N-dimethylamidino)phenyl)]-(2R,4R)-4-hydroxypyrrolidine-1,2-dicarboxamide, N-1-[(4-chlorophenyl)]-N-2-[(2-fluoro-4-(N,N-dimethyla-
midino)phenyl)-]-(2R,4R)-4-hydroxypyrrolidine-1,2-di-
carboxamide,
N-1-[(4-ethynylphenyl)]-N-2-[(2-fluoro-4-(N,N-dimethyla-
midino)phenyl)]-(2R,4R)-4-hydroxypyrrolidine-1,2-di-
carboxamide.

EXAMPLE 5

N-1-[(4-Chlorophenyl)]-N-2-[(4-(1-methyl-4,5-dihy-
dro-1H-imidazol-2-yl)phenyl)]-(2R,4R)-4-hydroxy-
pyrrolidine-1,2-dicarboxamide ("A5")

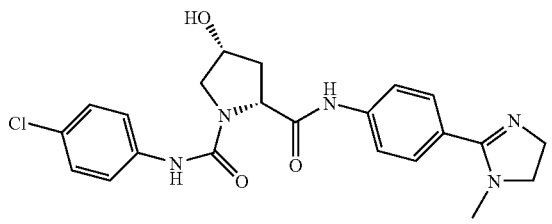

("A5")

Compound "8" is dissolved in dry methanol. 3 equivalents of N-methylethane-1,1-diamine are added, and the mixture is heated under reflux. After 1 hour, the mixture is subjected to conventional work-up, giving "A5".

The following compounds are obtained analogously
N-1-[(4-chlorophenyl)]-N-2-[(2-fluoro-4-(1-methyl-4,5-di-
hydro-1H-imidazol-2-yl)phenyl)]-(2R,4R)-4-hydroxy-
pyrrolidine-1,2-dicarboxamide,
N-1-[(4-ethynylphenyl)]-N-2-[(4-(1-methyl-4,5-dihydro-
1H-imidazol-2-yl)phenyl)]-(2R,4R)-4-hydroxypyrroli-
dine-1,2-dicarboxamide,
N-1-[(4-ethynylphenyl)]-N-2-[(2-fluoro-4-(1-methyl-4,5-
dihydro-1H-imidazol-2-yl)phenyl)]-(2R,4R)-4-hydroxy-
pyrrolidine-1,2-dicarboxamide.

The following examples relate to pharmaceutical compositions:

EXAMPLE A

Injection Vials

A solution of 100 g of an active ingredient of the formula I and 5 g of disodium hydrogenphosphate in 3 l of bidistilled water is adjusted to pH 6.5 using 2 N hydrochloric acid, sterile filtered, transferred into injection vials, lyophilised under sterile conditions and sealed under sterile conditions. Each injection vial contains 5 mg of active ingredient.

EXAMPLE B

Suppositories

A mixture of 20 g of an active ingredient of the formula I is melted with 100 g of soya lecithin and 1400 g of cocoa butter, poured into moulds and allowed to cool. Each suppository contains 20 mg of active ingredient.

EXAMPLE C

Solution

A solution is prepared from 1 g of an active ingredient of the formula I, 9.38 g of $NaH_2PO_4.2H_2O$, 28.48 g of $Na_2HPO_4.12H_2O$ and 0.1 g of benzalkonium chloride in 940 ml of bidistilled water. The pH is adjusted to 6.8, and the solution is made up to 1 l and sterilised by irradiation. This solution can be used in the form of eye drops.

EXAMPLE D

Ointment 500 mg of an active ingredient of the formula I are mixed with 99.5 g of Vaseline under aseptic conditions.

EXAMPLE E

Tablets

A mixture of 1 kg of active ingredient of the formula I, 4 kg of lactose, 1.2 kg of potato starch, 0.2 kg of talc and 0.1 kg of magnesium stearate is pressed to give tablets in a conventional manner in such a way that each tablet contains 10 mg of active ingredient.

EXAMPLE F

Coated Tablets

Tablets are pressed analogously to Example E and subsequently coated in a conventional manner with a coating of sucrose, potato starch, talc, tragacanth and dye.

EXAMPLE G

Capsules 2 kg of active ingredient of the formula I are introduced into hard gelatine capsules in a conventional manner in such a way that each capsule contains 20 mg of the active ingredient.

EXAMPLE H

Ampoules

A solution of 1 kg of active ingredient of the formula I in 60 l of bidistilled water is sterile filtered, transferred into ampoules, lyophilised under sterile conditions and sealed under sterile conditions. Each ampoule contains 10 mg of active ingredient.

The invention claimed is:
1. A compound of the formula
N-1-[(4-chlorophenyl)]-N-2-{[4-(2{dimethylaminom-
ethyl }phenyl)phenyl]-}-(2R,4R)-4-hydroxypyrroli-
dine-1,2-dicarboxamide,
N-1-[(4-ethynylphenyl)]-N-2-{[4-(2-
{dimethylaminomethyl}phenyl)-phenyl]}-(2R,4R)-4-
hydroxypyrrolidine-1,2-dicarboxamide,
N-1-[(4-chlorophenyl)]-N-2-{[2-fluoro-4-(2-{dimethy-
laminomethyl}-phenyl)phenyl]}-(2R,4R)-4-hydroxy-
pyrrolidine-1,2-dicarboxamide,
N-1-[(4-ethynylphenyl)]-N-2-{[2-fluoro-4-(2-{dimethy-
laminomethyl}-phenyl)phenyl]}-(2R,4R)-4-hydroxy-
pyrrolidine-1,2-dicarboxamide,
N-1-[(4-chlorophenyl)]-N-2-[(4-(2-dimethylaminometh-
ylimidazol-1-yl)-phenyl)]-(2R,4R)-4-hydroxypyrroli-
dine-1,2-dicarboxamide,
N-1-[(4-ethynylphenyl)]-N-2-[(4-(2-dimethylaminom-
ethyl-imidazol-1-yl)-phenyl)]-(2R,4R)-4-hydroxypyr-
rolidine-1,2-dicarboxamide,

N-1-[(4-chlorophenyl)]-N-2-[(2-fluoro-4-(2-dimethy-laminomethyl-imidazol -1-yl)phenyl)]-(2R,4R)-4-hydroxypyrrolidine-1,2-dicarboxamide,
N-1-[(4-ethynylphenyl)]-N-2-[(2-fluoro-4-(2-dimethylamino-methylimidazol-1-yl)phenyl)]-(2R,4R)-4-hydroxypyrrolidine-1,2-dicarboxamide,
N-1-[(4-chlorophenyl)]-N-2-[(4-(N,N-dimethylamidino)phenyl)]-(2R,4R)-4-hydroxypyrrolidine-1,2-dicarboxamide,
N-1-[(4-ethynylphenyl)]-N-2-[(4-(N,N-dimethylamidino)phenyl)]-(2R,4R)-4-hydroxypyrrolidine-1,2-dicarboxamide,
N-1-[(4-chlorophenyl)]-N-2-[(2-fluoro-4-(N,N-dimethylamidino)phenyl)]-(2R,4R)-4-hydroxypyrrolidine-1,2-dicarboxamide,
N-1-[(4-ethynylphenyl)]-N-2-[(2-fluoro-4-(N,N-dimethylamidino)phenyl)]-(2R,4R)-4-hydroxypyrrolidine-1,2-dicarboxamide,
N-1-[(4-chlorophenyl)]-N-2-[(4-(1-methyl-4,5-dihydro-1H-imidazol-2-yl)-phenyl)]-(2R,4R)-4-hydroxypyrrolidine-1,2-dicarboxamide,
N-1-[(4-chlorophenyl)]-N-2-[(2-fluoro-4-(1-methyl-4,5-dihydro-1H-imidazol-2-yl)phenyl)]-(2R,4R)-4-hydroxypyrrolidine-1,2-dicarboxamide,
N-1-[(4-ethynylphenyl)]-N-2-[(4-(1-methyl-4,5-dihydro-1H-imidazol-2-yl)-phenyl)]-(2R,4R)-4-hydroxypyrrolidine-1,2-dicarboxamide, N-1-[(4-ethynylphenyl)]-N-2-[(2-fluoro-4-(1-methyl-4,5-dihydro-1H-imidazol-2-yl)phenyl)]-(2R,4R)-4-hydroxypyrrolidine-1,2-dicarboxamide,
or pharmaceutically usable derivatives, salts or stereoisomers thereof, including mixtures thereof in all ratios.

2. Process for the preparation of compounds of the formula I

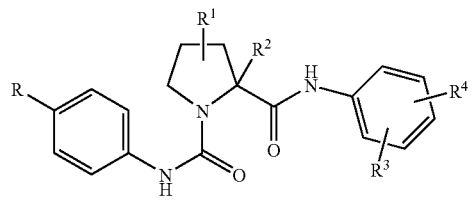

in which
R denotes Hal, —C≡C—H, —C≡C-A or OA,
R$^1$ denotes H, =O, Hal, A, OH, OA, A-COO—, Ph-(CH$_2$)$_n$—COO—, cycloalkyl-(CH$_2$)$_n$—COO—, A-CONH—, A-CONA-, Ph-CONA-, N$_3$, NH$_2$, NO$_2$, CN, COOH, COOA, CONH$_2$, CONHA, CON(A)$_2$, O-allyl, O-propargyl, O-benzyl, =N—OH, =N—OA or =CF$_2$,
R$^2$ denotes H or A,
Ph denotes phenyl which is unsubstituted or mono-, di- or trisub -stituted by A, OA, OH or Hal,
R$^3$ denotes H, Hal or A,
R$^4$ denotes —C$_6$H$_4$—(CH$_2$)$_n$—NR$^5$R$^{5'}$, —C(=NR$^5$)NR$^5$R$^{5'}$,

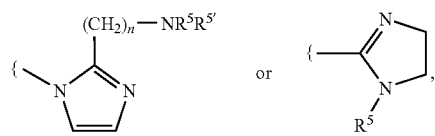

R$^5$, R$^5$ ' each, independently of one another, denote H or A,

A denotes unbranched, branched or cyclic alkyl having 1-12 C atoms, in which, in addition, 1-7 H atoms may be replaced by F and/or chlorine,
Hal denotes F, Cl, Br or I,
n denotes 0, 1, 2 or 3,
or pharmaceutically usable derivatives, salts and stereoisomers thereof, comprising reacting
a) a compound of the formula II

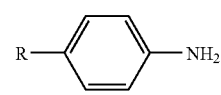

with a chloroformate derivative to give an intermediate carbamate derivative, subsequently reacting said intermediate with a compound of the formula III

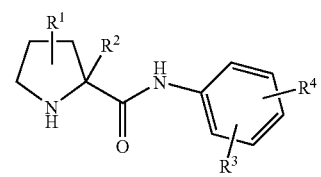

or
b) reacting a compound of the formula III with a compound of the formula IV

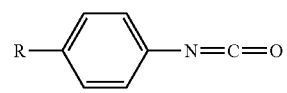

or
c) reacting a compound of the formula V

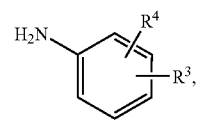

with a compound of the formula VI

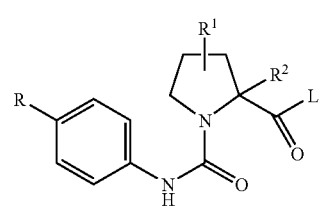

in which
L denotes Cl, Br, I or a free or reactively functionally modified OH group
and/or converting
a base or acid of the formula I into one of its salts.

3. A pharmaceutical composition comprising at least one compound according to Claim 1 and/or pharmaceutical usable derivatives, salts and stereoisomers thereof, including mixtures thereof in all ratios, and pharmaceutically acceptable excipients and/or adjuvants.

4. A method for the treatment of thromboses, myocardial infraction, arteriosclerosis, inflammation, apoplexy, angina pectoris, restenosis after angioplasty, claudicatio intermittens, migraine, tinnitus, tumours, tumour diseases and/of tumour metastses, comprising administered to a host in need thereof an effective amount of a compound of claim 1 and/or pharmaceutically useable derivatives, salts or stereoisomers thereof.

5. A compound according to claim 1, wherein said compound is N-1-[(4-chlorophenyl)]-N-2-{[4-(2-{dimethylaminomethyl}phenyl)phenyl]}-(2R,4R)-4-hydroxypyrrolidine-1,2-dicarboxamide, or a pharmaceutically usable salt thereof.

6. A compound according to claim 1, wherein said compound is N-1-[(4-ethynylphenyl)]-N-2-{[4-(2{dimethylaminomethyl}phenyl)phenyl]}1-(2R,4R)-4-hydroxypyrrolidine-1,2-dicarboxamide, or a pharmaceutically usable salt thereof.

7. A compound according to claim 1, wherein said compound is N-1-[(4-chlorophenyl)]-N-2-{[2-fluoro-4-(2-{dimethylaminomethyl}phenyl)phenyl]}-(2R,4R)-4-hydroxypyrrolidine-1,2-dicarboxamide, or a pharmaceutically usable salt thereof.

8. A compound according to claim 1, wherein said compound is N-1-[(4-ethynylphenyl)]-N-2-{[2-fluoro-4-(2-{dimethylaminomethyl}phenyl)phenyl]}-(2R,4R)-4-hydroxypyrrolidine-1,2-dicarboxamide, or a pharmaceutically usable salt thereof.

9. A compound according to claim 1, wherein said compound is N-1-[(4-chlorophenyl)]-N-2-[(4-(2-dimethylaminomethylimidazol-1-yl)phenyl)]-(2R,4R)-4-hydroxypyrrolidine-1,2-dicarboxamide, or a pharmaceutically usable salt thereof.

10. A compound according to claim 1, wherein said compound is N-1-[(4-ethynylphenyl)]-N-2-[(4-(2-dimethylaminomethyl-imidazol-1-yl)phenyl)]-(2R,4R)-4-hydroxypyrrolidine-1,2-dicarboxamide, or a pharmaceutically usable salt thereof.

11. A compound according to claim 1, wherein said compound is N-1-[(4-chlorophenyl)]-N-2-[(2-fluoro-4-(2-dimethylaminomethyl-imidazol-1-yl)phenyl)]-(2R,4R)-4-hydroxypyrrolidine-1,2-dicarboxamide, or a pharmaceutically usable salt thereof.

12. A compound according to claim 1, wherein said compound is N-1-[(4-ethynylphenyl)]-N-2-[(2-fluoro-4-(2-dimethylaminomethylimidazol-1-yl)phenyl)]-(2R,4R)-4-hydroxypyrrolidine-1,2-dicarboxamide, or a pharmaceutically usable salt thereof.

13. A compound according to claim 1, wherein said compound is N-1-[(4-chlorophenyl)]-N-2-[(4-(N,N-dimethylamidino)phenyl)]-(2R,4R)-4-hydroxypyrrolidine-1,2-dicarboxamide, or a pharmaceutically usable salt thereof.

14. A compound according to claim 1, wherein said compound is N-1-[(4-ethynylphenyl)]-N-2-[(4-(N,N-dimethylamidino)phenyl)]-(2R,4R)-4-hydroxypyrrolidine-1,2-dicarboxamide, or a pharmaceutically usable salt thereof.

15. A compound according to claim 1, wherein said compound is N-1-[(4-chlorophenyl)]-N-2-[(2-fluoro-4-(N,N-dimethylamidino)phenyl)]-(2R,4R)-4-hydroxypyrrolidine-1,2-dicarboxamide, or a pharmaceutically usable salt thereof.

16. A compound according to claim 1, wherein said compound is N-1-[(4-ethynylphenyl)]-N-2-[(2-fluoro-4-(N,N-dimethylamidino)phenyl)]-(2R,4R)-4-hydroxypyrrolidine-1,2-dicarboxamide, or a pharmaceutically usable salt thereof.

17. A compound according to claim 1, wherein said compound is N-1-[(4-chlorophenyl)]-N-2-[(4-(1-methyl-4,5-dihydro-1H-imidazol-2-yl)phenyl)]-(2R,4R)-4-hydroxypyrrolidine-1,2-dicarboxamide, or a pharmaceutically usable salt thereof.

18. A compound according to claim 1, wherein said compound is N-1-[(4-chlorophenyl)]-N-2-[(2-fluoro-4-(1-methyl-4,5-dihydro-1H-imidazol-2-yl)phenyl)]-(2R,4R)-4-hydroxypyrrolidine-1,2-dicarboxamide, or a pharmaceutically usable salt thereof.

19. A compound according to claim 1, wherein said compound is N-1-[(4-ethynylphenyl)]-N-2-[(4-(1-methyl-4,5-dihydro-1H-imidazol-2-yl)phenyl)]-(2R,4R)-4-hydroxypyrrolidine-1,2-dicarboxamide, or a pharmaceutically usable salt thereof.

20. A compound according to claim 1, wherein said compound is N-1-[(4-ethynylphenyl)]-N-2-[(2-fluoro-4-(1-methyl-4,5-dihydro-1H-imidazol-2-yl)phenyl)]-(2R,4R)-4-hydroxypyrrolidine-1,2-dicarboxamide, or a pharmaceutically usable salt thereof.

* * * * *